United States Patent [19]

Steer

[11] Patent Number: 4,723,951
[45] Date of Patent: Feb. 9, 1988

[54] GAS FILTER ARRANGEMENT FOR OSTOMY OR ILEOSTOMY BAGS

[75] Inventor: Peter L. Steer, Surrey, England

[73] Assignee: Craig Medical Products Ltd., Sussex, England

[21] Appl. No.: 876,012

[22] Filed: Jun. 19, 1986

[30] Foreign Application Priority Data

Jul. 15, 1985 [GB] United Kingdom ............... 85-17805

[51] Int. Cl.⁴ ............................................. A61F 5/44
[52] U.S. Cl. ...................................... 604/333; 55/511; 55/505
[58] Field of Search ................. 604/333, 359; 55/507, 55/505, 524, 501, 511, 487; 383/102, 103

[56] References Cited

U.S. PATENT DOCUMENTS

| | | | |
|---|---|---|---|
| Re. 29,453 | 10/1977 | Weddle | 128/283 |
| 2,946,502 | 7/1960 | Metzger | 383/103 |
| 3,039,464 | 6/1962 | Galindo | 128/283 |
| 3,055,368 | 9/1962 | Baxter | 128/283 |
| 3,081,771 | 3/1963 | Lee | 128/283 |
| 3,121,021 | 2/1964 | Copeland | 117/122 |
| 3,339,546 | 9/1967 | Chen | 128/156 |
| 3,522,807 | 8/1970 | Millenbach | 128/283 |
| 3,604,421 | 9/1971 | Pizzella | 128/DIG. 24 |
| 3,690,320 | 9/1972 | Riely | 128/283 |
| 3,734,096 | 5/1973 | Millenbach | |
| 3,865,109 | 2/1975 | Elmore et al. | 128/283 |
| 4,095,599 | 6/1978 | Simonet-Haibe | 128/283 |
| 4,111,205 | 9/1978 | Nemeth | 128/284 |
| 4,192,785 | 3/1980 | Chen et al. | 128/283 |
| 4,213,458 | 7/1980 | Nolan et al. | 128/283 |
| 4,393,080 | 7/1983 | Pawelchak et al. | 428/355 |
| 4,449,970 | 5/1984 | Bevan et al. | 604/333 |
| 4,450,845 | 5/1984 | Engel | 128/743 |
| 4,488,557 | 12/1984 | Engel | 128/635 |

FOREIGN PATENT DOCUMENTS

| | | |
|---|---|---|
| 0081907 | 11/1982 | European Pat. Off. . |
| 2396541 | 3/1979 | France . |
| 1256866 | 12/1971 | United Kingdom . |
| 1379464 | 1/1975 | United Kingdom . |
| 1405032 | 9/1975 | United Kingdom . |
| 1550960 | 8/1979 | United Kingdom . |
| 2031282 | 4/1980 | United Kingdom . |
| 1568860 | 6/1980 | United Kingdom . |
| 1571657 | 7/1980 | United Kingdom . |
| 2053718 | 2/1981 | United Kingdom . |
| 2058011 | 4/1981 | United Kingdom . |
| 2083760 | 3/1982 | United Kingdom . |
| 2116433 | 9/1983 | United Kingdom . |
| 2119654 | 11/1983 | United Kingdom . |
| 2122090 | 1/1984 | United Kingdom . |
| 2145334 | 3/1985 | United Kingdom . |
| 2149306 | 6/1985 | United Kingdom . |

OTHER PUBLICATIONS

U.S. Ser. No. 870,592 filed on 6/4/86 for "Attachment Assembly for Use On The Human Skin".
U.S. Ser. No. 681,176, filed 12/13/84 entitled "Ostomy Appliance with Improved Attachment Means".

*Primary Examiner*—C. Fred Rosenbaum
*Assistant Examiner*—J. L. Kruter
*Attorney, Agent, or Firm*—Lawrence S. Levinson; Robert E. Lee, Jr.

[57] ABSTRACT

An ostomy bag has a filter attached to it by a series of plural sequentially peelable adhesive annuli.

6 Claims, 5 Drawing Figures

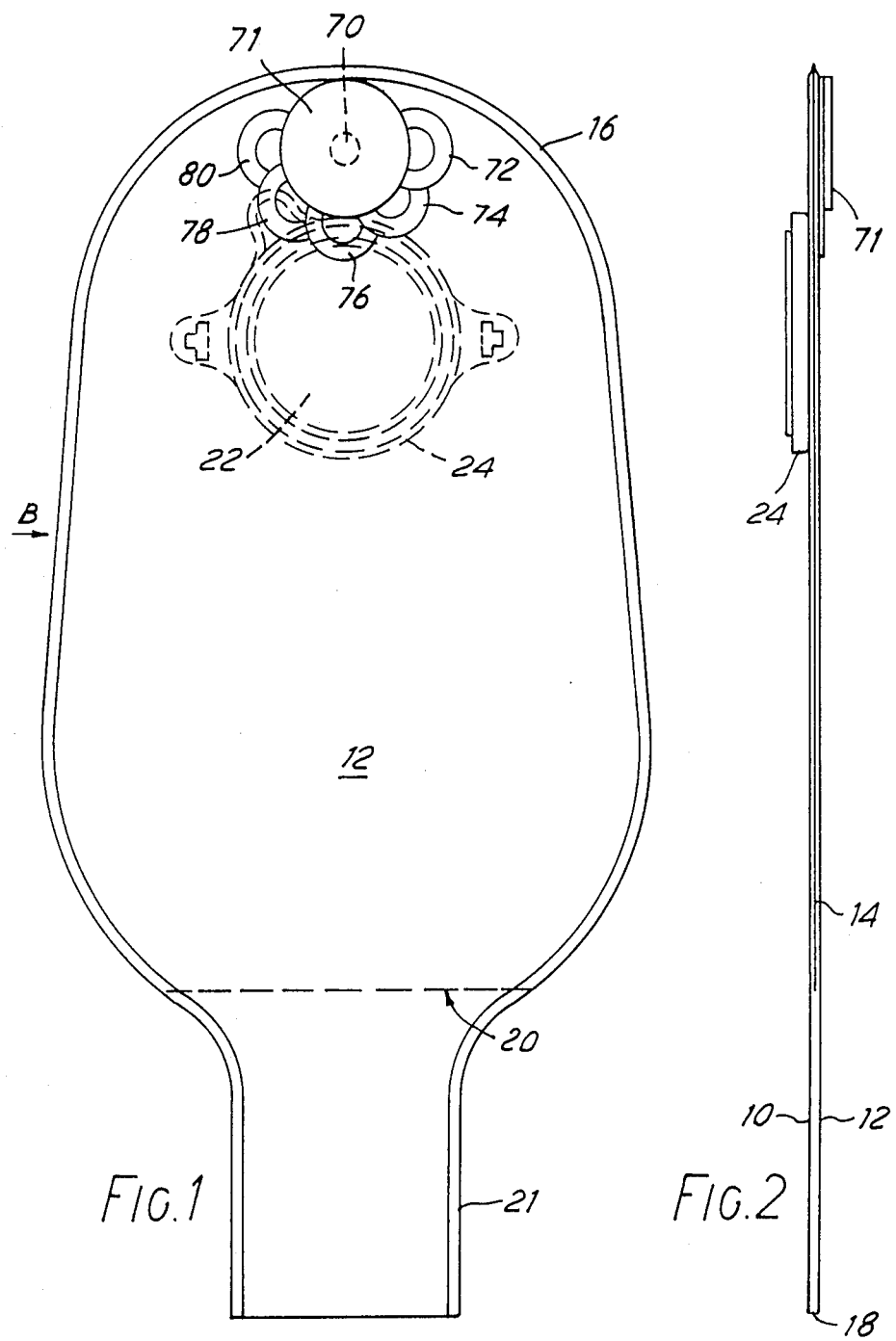

GAS FILTER ARRANGEMENT FOR OSTOMY OR ILEOSTOMY BAGS

BACKGROUND OF THE INVENTION

This invention relates to a gas filter arrangement for ostomy bags, and to ostomy bags, particularly ileostomy bags, including gas filter arrangements.

There have been numerous prior proposals for gas filters for ostomy bags, of which the following patent specifications can be mentioned as a representative selection: U.K. No. 2,053,718; U.K. No. 2,122,090; U.K. No. 2,116,433; U.K. No. 2,031,282; U.K. No. 1,405,032; U.K. No. 1,550,960; U.K. No. 2,145,334; U.K. No. 2,149,306; U.K. No. 2,083,760; U.K. No. 1,379,464; U.S. Pat. Nos. 3,690,320; 3,865,109.

Particularly with ileostomy bags, one of the problems in bags having a filter is that the filter may become blocked due to the discharge being part-liquid, part-solid or of a slurry-like nature. Efforts have been made to design bags and pouches which meet the apparently conflicting requirements of preventing the discharge from reaching the filter and yet allowing gases within the bag to readily reach the filter. To the best of the applicant's knowledge and belief, there has been no satisfactory solution despite numerous efforts in the prior art, to the problem of allowing a wearer to make a quick and easy replacement of a filter which has become ineffective. Provision is made in various prior proposals for changing a used filter for a new filter. The constructions proposed are often complex, expensive to manufacture and awkward to manipulate. For example, U.K. Application No. 2 031 282 discloses a filter 6 placed over a vent hole in a bag. This filter would appear to be permanently attached to the bag, so, when its effectiveness reduces, a new bag would be required. U.K. Pat. No. 2,083,760 and U.S. Pat. No. 4,449,970 disclose a flatus filter which is folded over a top edge to cover perforations in each of two walls of a bag. With this arrangement one can remove an ineffective filter and replace it with a new filter but the manipulation necessary to peel or tear off the old filter and fold over and fit the new filter properly aligned with pinholes in the bag walls which are probably not easily visible is a difficult or impossible task for many users.

SUMMARY OF THE INVENTION

In accordance with the present invention, an ostomy bag has a filter attached to it by a series of sequentially peelable adhesive annuli.

The invention also comprehends a stack of adhesive annuli which are sequentially peelable and which are for use with an ostomy bag or pouch (in particular an ileostomy bag).

The invention also provides a method of changing a flatus filter on an ostomy bag which comprises peeling off one adhesively-attached filter in such a way as to expose an adhesive surface on an annulus which is lower down in a stack of adhesive annuli, and sticking a new filter on to the adhesive so exposed.

The bag may be constructed as a two-compartment bag, there being an intermediate dividing wall constituted by a plastics film which is partly or wholly perforated. The perforation holes are preferably circular in shape (although they may be of any shape) and they preferably have a maximum dimension (a diameter in the case of a circular hole) which is in the range of 2–15 thousandths of an inch, i.e. substantially 0.05 to 0.38 millimeters. The purpose of this intervening wall is to inhibit access of the liquid or slurry-like faecal material to the filter but to nevertheless allow flatus gases to pass through the intervening wall and reach the filter. The intervening wall may be secured in a position by the same peripheral weld which joins the bag walls together. In this context, it will be understood that it is conventional for ostomy bags to be made of front and rear walls of plastics film superposed one upon the other and joined together around the periphery (or around the major part of the periphery) by a weld. This construction and procedure being conventional, it need not be further described; reference may be had for example to British Patent Specification No. 2,058,011 or 2,031,282.

The intervening wall may be perforated over its whole area or over its upper region only. It may extend any desired distance downwardly within the bag; that is, it may extend completely to the bottom of the bag, or merely to a lower region of the bag, near to the bag outlet, or approximately half-way down the bag. Its lower edge may if desired be intermittently welded to the bag front and rear walls. An intermediate wall configuration similar to that shown at 30,32 in FIG. 2 of U.K. published patent application No. 2, 149 306 may be employed. The plastics film of the intervening wall may be the same as the inner and outer bag walls, for example it may be made of a polymer, e.g. ethylene vinyl acetate or polyvinylidene chloride or it may be a laminate whose layers may by EVA, PVDC, and/or other plastics film materials conventionally used for this purpose. The perforations may be provided by a "needling" operation.

An advantage of the present invention over the prior art is that action can easily be taken, without awkward manipulation, and without removing the bag, to ensure that a new filter is exposed to the exiting flatus gases. This is done by peeling off the filter (and the uppermost adhesive annulus attached thereto) from the bag by separating this annulus from the next one of the sequence, and then placing a new filter on the freshly exposed adhesive of the next underlying annulus.

The invention will be better understood from the following description of illustrative embodiments thereof, given by way of example with reference to the accompanying drawings in which:

BRIEF DESCRIPTION OF THE DRAWINGS

FIG. 1 is a front view of an ileostomy bag according to the invention and including a filter arrangement including a series of sequentially peelable adhesive annuli, and FIG. 2 is a side view looking in the direction of the arrow B in FIG. 1.

DETAILED DESCRIPTION OF THE DRAWINGS

Figure 3A:
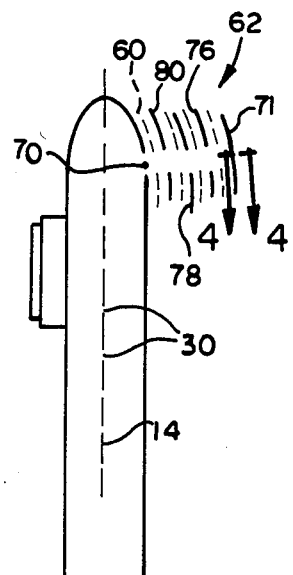
FIGS. 3A and 3B are diagrammatic vertical sectional views of the ileostomy bag of FIG. 1 showing first and second arrangements of the filter and series of sequentially peelable adhesive annuli.
Figure 3B:
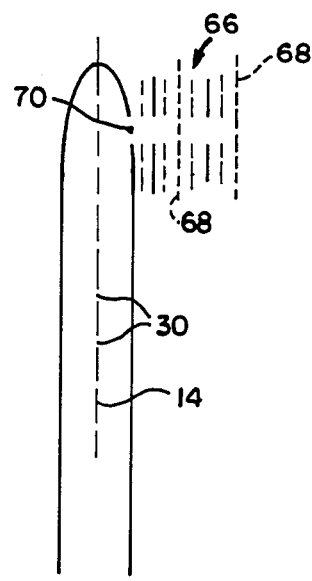

In the drawings, like parts are denoted by like reference numerals.

The illeostomy bag illustrated in FIGS. 1 and 2 has a front wall 10, a rear wall 12 and an intervening wall 14 with circular perforation holes 30. These walls are secured together by a peripheral weld 16. The bag so produced has a bottom outlet 18, and the intervening wall does not extend completely to the bottom of the bag. Its bottom edge is indicated at 20.

A stomal orifice 22 is provided in the rear wall 12, and this is surrounded by an ostomy coupling element 24. The coupling element 24 is preferably of the kind described and claimed in British Patent No. 1,571,657 and in counterpart patents and patent applications throughout the world. However, other forms of ostomy coupling elements may be employed. The purpose of such an element is, as is well known, to connect the bag to a pad or face plate or surgical grade adhesive material which is attached to the peristomal area of the person wearing the bag.

The front wall 10 has a hole 70 in its upper region. An annular region surrounding the hole is covered with adhesive 60. Placed upon this adhesive is a bottom annulus of a series or stack 62 of sequentially removable annuli. Each of these has adhesive on it and in use the bottom one is the last to be removed. Each of these adhesive annuli has a gripping tab constituted by a circular portion integral with the adhesive annulus. That is to say, each adhesive annulus resembles a FIG. 8 in shape, one loop of the 8 being the gripping tab and the other loop being constituted by an annulus bearing adhesive with the center hole of the other loop being aligned with the hole 70. In FIG. 1, the gripping tab loops are seen at 72, 74, 76, 78 and 80, 80 being the bottom and last-removed annulus. In FIG. 3A only three annuli are shown for illustration purposes with gripping tabs 80, 78 and 76. A filter 71 is placed on top of the top annulus 72, and secured thereto by adhesive.

In use, when wearing the ileostomy bag according to FIGS. 1 and 2, and when the wearer believes that the filter may need replacement, he or she grasps the tab 72 and separates it from the remaining tabs by placing a thumb or finger on tab 74 and pulling tab 72 upwards. In this way, the filter 71 is removed, and thereafter a new filter is pressed straight on to the exposed fresh adhesive on annulus 74, this having been exposed by removal of the annulus 72. In a similar way, freshly exposed adhesive annuli 76, 78 and 80 of the stack 71 can be used in turn to attach three new filters without the ileostomy bag being removed from the wearer.

The bottom edge of the intervening wall is seen at 20 in FIG. 1 but this wall may extend completely to the bottom of the outlet position 21 of the bag, if desired.

As an alternative to using annuli which have adhesive on one side, annuli which have adhesive on both sides designated generally 66 may be used interleaved with perforated discs or annuli of release material 68, e.g. silicone-coated paper or plastics film. Release annuli may alternatively be interleaved with single sided adhesive annuli.

In this specification, the words "annulus" and "annuli" are used without strict geometrical connotation. These words are intended to cover any shape of element having a central hole, this being necessary to allow passage of flatus gases, surrounded by a closed loop surface upon which adhesive can be carried.

While the gripping tabs have been illustrated as having a substantially circular shape, it will be realized that the invention can be carried into practice, and its advantages achieved, with tabs of various shapes.

Any suitable filter may be employed as the filter 71 although a filter as disclosed in our U.K. Patent Application No. 8503 749 is preferred.

In accordance with the description of a suitable filter taken from pages 2, 4 and 5 of U.K. Patent Application No. 85 03749, the gas filter illustrated in FIG. 4 has a first membrane 40, a second membrane 42, and between these is sandwiched a pad 44 of carbon impregnated polyurethane foam.

Figure 4:
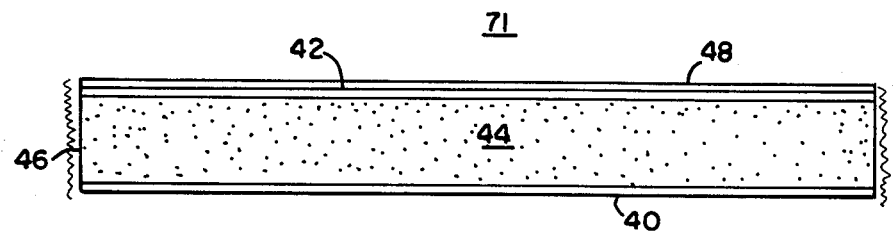
FIG. 4 is a schematic cross section, not to scale, taken in a vertical axial plane taken along the lines and arrows 4—4 in FIG. 3A through one embodiment of a filter suitable for the present invention.

These three parts are secured together in any convenient way so that they are integrated into a single unitary gas filter. The edges are sealed so as to prevent gas escape by a sealant such as a cement 46 around the periphery. A thin layer 48 of water-repellent material (its thickness is exaggerated for clarity in FIG. 4) covers the upper surface (as seen in FIG. 4) of the microporous membrane 42. The thickness of the layer 48 is preferably only a few hundredths of a millimeter.

The pad 44 is reticulated polyurethane foam having the following characteristics:

Density: 27–30 KG/M$^3$
Compression resistance: 3.4–4.6 KPA
Ultimate elongation: 350%
Tensile strength: 200 KPA
Tear strength: 6N/cm
Porosity: 65–85 (PPI)

The microporous membrane 40 and 42 are each a polyurethane film or foil 0.10 to 0.15 mm thick having controlled-size microporous holes therein. The layer 18 is water-repellent polytetrafluroethylene (PTFE).

I claim:

1. An ostomy bag including a vent whereby flatus gases can escape from the bag, a gas filter with the vent for filtering the flatus gases escaping from the bag, and a series of plural sequentially peelable adhesive annuli means superimposed on one another and attaching said filter to the bag.

2. A bag according to claim 1 in which each annulus has a gripping tab.

3. A bag according to claim 1 including an intervening wall perforated with a plurality of holes.

4. A bag according to claim 3 in which the intervening wall is secured in position by the same peripheral weld which joins the bag front and rear wall together.

5. A method of changing a flatus filter adhesively attached on an ostomy bag by a stack of plural superimposed adhesive annuli which comprises peeling off the top one of adhesive annuli of the stack to which the filter is adhesively attached to expose an adhesive surface on an annulus which is lower down in the stack of adhesive annuli, providing a new filter, and sticking the new filter to the adhesive surface so exposed.

6. An ostomy bag including a vent whereby flatus gases can escape from the bag, a gas filter associated with the vent for filtering the flatus gases escaping from the bag, and a series of plural sequentially superimposed peelable annuli, each with an adhesive coating on both sides, said series including perforated discs of release material interleaved with the adhesive annuli.

* * * * *